United States Patent
Niederberger et al.

(10) Patent No.: US 8,838,037 B2
(45) Date of Patent: Sep. 16, 2014

(54) MOBILE PHONE WITH HUMIDITY SENSOR

(75) Inventors: Dominik Niederberger, Zürich (CH); Johannes Schumm, Zürich (CH); Pascal Gerner, Zürich (CH); Markus Graf, Zürich (CH)

(73) Assignee: Sensirion AG, Stafa (CH)

( * ) Notice: Subject to any disclaimer, the term of this patent is extended or adjusted under 35 U.S.C. 154(b) by 0 days.

(21) Appl. No.: 13/398,439

(22) Filed: Feb. 16, 2012

(65) Prior Publication Data
US 2012/0231841 A1   Sep. 13, 2012

(30) Foreign Application Priority Data
Mar. 9, 2011   (EP) ..................................... 11001945

(51) Int. Cl.
*H04B 17/00* (2006.01)
*H04M 1/21* (2006.01)

(52) U.S. Cl.
CPC ............ *H04M 1/21* (2013.01); *H04M 2250/12* (2013.01)
USPC ........................................ 455/67.11; 370/338

(58) Field of Classification Search
CPC .................................................. H04M 2250/12
USPC ............................................ 455/550.1, 556.1
See application file for complete search history.

(56) References Cited

U.S. PATENT DOCUMENTS

| | | | |
|---|---|---|---|
| 2005/0009195 A1 | 1/2005 | Wang | |
| 2005/0030724 A1 | 2/2005 | Ryhanen | |
| 2006/0141945 A1 * | 6/2006 | Korhonen et al. | 455/90.1 |
| 2006/0248946 A1 | 11/2006 | Howell et al. | |
| 2007/0116596 A1 | 5/2007 | Duranton | |
| 2007/0185392 A1 * | 8/2007 | Sherman et al. | 600/306 |
| 2008/0044939 A1 | 2/2008 | Nassiopoulou et al. | |
| 2008/0064413 A1 * | 3/2008 | Breed | 455/456.1 |
| 2008/0177404 A1 | 7/2008 | Bonnat | |
| 2008/0250847 A1 | 10/2008 | Kitani et al. | |
| 2009/0215439 A1 | 8/2009 | Hamilton et al. | |
| 2010/0015992 A1 | 1/2010 | Wakefield | |
| 2010/0156663 A1 | 6/2010 | Pal | |

FOREIGN PATENT DOCUMENTS

| | | |
|---|---|---|
| CN | 2857356 | 1/2007 |
| CN | 2867738 | 2/2007 |
| DE | 3817504 | 5/1987 |
| EP | 2469270 | 6/2012 |
| EP | 2479892 | 7/2012 |

(Continued)

OTHER PUBLICATIONS

XP-002413991, C701 802.15.4 Zigbee, ready Wirelss Sensor Module, Craition Electronics R&D, Sep. 1, 2004.

(Continued)

*Primary Examiner* — Marcos Batista
(74) *Attorney, Agent, or Firm* — Cooper & Dunham LLP

(57) ABSTRACT

A mobile phone comprises a casing and a cavity in the casing. A humidity sensor is arranged for measuring a humidity in the cavity. In response to a trigger, a control unit analyzes a humidity signal supplied by the humidity sensor. A result of the analysis is presented via an output unit. Such device allows for measuring a humidity of a user's skin in case the user covers a window in the casing connected to the cavity by a body part.

14 Claims, 3 Drawing Sheets

(56) References Cited

FOREIGN PATENT DOCUMENTS

| | | | |
|---|---|---|---|
| EP | 2479963 | 7/2012 | |
| GB | 2177216 | 1/1987 | |
| JP | 08125726 | 5/1996 | |
| JP | 2010160286 | 7/2010 | |
| KR | 20040103297 | 12/2004 | |
| KR | 1020050097216 | 10/2005 | |
| KR | 100690638 | 2/2007 | |
| WO | 0212884 | 2/2002 | |
| WO | 0222007 A2 | 3/2002 | |
| WO | 0222007 A3 | 3/2002 | |
| WO | 2004/066194 | 8/2004 | |
| WO | 2005/092294 | 9/2005 | |
| WO | 2005/120333 | 12/2005 | |
| WO | 2007/036922 | 4/2007 | |
| WO | WO 2010091852 A1 * | 8/2010 | ............. A61M 1/36 |

OTHER PUBLICATIONS

U.S. Appl. No. 13/358,612, filed Jan. 26, 2012, titled Portable Electronic Device.

Peter Rojas, The Cellphone Skin Analyzer, Apr. 12, 2012.

Frauenhofer Institut Zuverlassigkeit und Mikrointegration—Effiziente Technologien fur Sensoren und Display, Apr. 12, 2012 with partial English translation.

Frank Zuther Hautschutz: Die Fluroeszenzmethode von Dermalux als Unterweisungshilfe fur Beschaftigte KBD GmbH, Ernahrung Aktuell Mai/Juni 2011 with partial English translation.

Moist Sense—Easily check the skin's moisture content, p. 32-33, 2009.

Ting-Hsiang Huang et al., A Device for Skin Moisture and Environment Humidity Detection, 5 pages, Apr. 12, 2012.

RM Gee et al., Tracable Calibrations for Water Vapour Flux Instruments—5th International Symposium on Humidity and Moisture—ISHM 2006 Brazil, May 2-5, 2006—Rio de Janeiro, Brazil.

F-02C Instruction Manual '10.11 docomo Style Series, Nov. 2011, available at http://www.nttdocomo.co.jp/english/binary/pdf/support/trouble/manual/download/f02c/F-02C_E_All.pdf.

"Fujitsu Introduces docomo Style series™ F-02C", Nov. 22, 2010, available at http://www.fujitsu.com/global/news/pr/archives/month/2010/20101122-01.html.

Honeywell HIH-4030/31 Series Humidity Sensors, Mar. 2008, available at http://sensing.honeywell.com/index.php?ci_id=51625.

Performance of the Vaisala RS80A/H and R590 Humicap Sensors and the Meteolabor 'Snow White' Chilled-Mirror Hygrometer in Paramaribo, Suriname in Journal of Atmospheric and Oceanic Technology vol. 23, Nov. 2006 pp. 1506-1518, by Ge Verver et.

Stefano Zampolli et al., "Ultra-low-power Components for an RFID Tag with Physical and Chemical Sensors", Microsyst Technol, (2008) 14: 581-588.

A. Koll et al., "A Flip-Chip Packaged CMOS Chemical Microsystem for Detection of Volatile Organic Compounds", Part of the SPIE Conference on Smart Electronics and MEMS, San Diego, CA, Mar. 1998, 223-232.

David J. Nagel, "Microsensor Clusters", Elsevier, Microelectronics Journal 33, (2002), 107-119.

English Language Translation of Korean Patent Publication No. 10-0690638, published Feb. 27, 2007.

* cited by examiner

MOBILE PHONE WITH HUMIDITY SENSOR

CROSS REFERENCE TO RELATED APPLICATIONS

This application claims the priority of European Patent Application 11001945.2, filed on Mar. 9, 2011, the disclosure of which is incorporated herein by reference in its entirety.

BACKGROUND OF THE INVENTION

The present invention relates to a mobile phone, to a method for operating a mobile phone, and to a corresponding computer program element.

Miniaturization and the enhancement of wireless technologies have enabled mobile phones to act as portable electronic multi-functional devices rather than as bare telephones.

BRIEF SUMMARY OF THE INVENTION

The problem to be solved by the present invention is to determine a health related parameter by means of a mobile phone.

This problem is solved by a mobile phone according to the features of claim 1. The mobile phone comprises a casing and a cavity in the casing. A humidity sensor is arranged for measuring a humidity in the cavity. A control unit is provided for analyzing a humidity signal supplied by the humidity sensor. An output unit is provided for presenting a result of the analysis.

The present mobile phone may act as a measuring and analyzing device with respect to the humidity of a user's skin. In such sense, the mobile phone may supply the user with information on his/her skin status such that the user may take cosmetic and/or health related measures subject to the results displayed.

It is noted that the arrangement of the cavity and the humidity sensor in the mobile phone is of a kind that a trans-epidermal water loss through the user's skin into the cavity may occur when an access to the cavity such as a window is covered by a body part of the user. The trans-epidermal water loss through the user's skin manifests in an evaporation of humidity into the cavity thereby increasing the humidity in the cavity. In the present embodiment, the cavity provides a space filled with air which accepts a trans-epidermal water loss in form of humidity filling such limited air volume. The cavity preferably is formed and arranged such that when the window is covered by the body part, the cavity is hermetically sealed resulting in the air volume being enriched in humidity which air may not leak into the environment neither via the window which is covered by the body part nor through cavity walls into an interior of the mobile phone which cavity walls preferably are leak-proof.

In a preferred embodiment, the humidity sensor delivers a humidity signal representing the relative humidity. The relative humidity is defined by the absolute humidity divided by the maximum humidity the air may accept. The humidity signal may be subject to treatment prior to being supplied to the control unit or prior to being analyzed in the control unit. Such treatment may include one or more of filtering, amplifying, compensating for undesired effects, dynamically compensating, building of any derivative, without limitation. Still, and irrespective of such treatment, the signal supplied to the control unit or the signal being analyzed there is considered as a humidity signal. In another embodiment, any such signal treatment may be considered as part of the analysis when executed in the control unit.

The humidity sensor preferably is a sensor of the kind that detects water molecules present in the air around the humidity sensor. In a preferred embodiment, the humidity sensor comprises a layer made from ceramics or a polymer. Such material may allow water molecules to enter the layer which results in a modified capacitance to be detected by electrodes used to determine the capacitance of the layer.

In a preferred embodiment, rather than analyzing the pure humidity levels in the corresponding humidity signal, the characteristic of the humidity signal over time is exploited i.e. its dynamics. In the analysis, it may be made use of such dynamics alone, or in combination with the humidity level. In a very preferred embodiment, the control unit is adapted for determining a change of the humidity signal by way of building a derivative of first or higher order of the humidity signal, or, for example, by way of determining a change of the humidity signal within a given time interval. In particular, an increase or decrease of the humidity signal may be classified. For such purpose, the increase or decrease may be compared to one or more thresholds. By suitably selecting the one or more thresholds, a meaningful classification as to the user's skin properties may be implemented. A start of the measurement and/or analysis may be triggered by the user pressing a key, a touch key or activating any other suitable input device. Preferably, a humidity level is measured in response to such trigger event and is recorded and used as a reference humidity value for one or more subsequently measured humidity values.

The window may be an opening solely assigned to the humidity sensor, or it may be an opening already existing in the electronic device, such as an opening for a microphone of a mobile phone. In such case, it may be beneficial if structural adaptations are implemented for building a cavity underneath the microphone opening or elsewhere for the subject purpose.

According to another aspect of the present invention, a method is provided for operating a mobile phone. In response to a trigger a humidity signal supplied by a humidity sensor arranged in a cavity of a casing of the mobile phone is analyzed. A result of the analysis is presented via an output unit of the mobile phone.

According to a further aspect of the present invention, a computer-readable medium is provided.

Other advantageous embodiments are listed in the dependent claims as well as in the description below.

The described embodiments similarly pertain to the device, the method and the computer program element. Synergetic effects may arise from different combinations of the embodiments although they might not be described in detail.

BRIEF DESCRIPTION OF THE DRAWINGS

The embodiments defined above and further aspects, features and advantages of the present invention can also be derived from the examples of embodiments to be described hereinafter and are explained with reference to the drawings. In the drawings the figures illustrate in FIG. 1 a schematic diagram of a mobile phone according to an embodiment of the present invention, FIG. 2 side cuts of a cavity in a casing of the mobile phone along lines A-A in FIG. 1, in two usage scenarios a) and b), FIG. 3 a side cut of a cavity in a casing of a mobile phone according to another embodiment of the present invention, FIG. 4 a block diagram of a mobile phone according to an embodiment of the present invention, FIG. 5 another block diagram of a mobile phone according to an embodiment of the present invention, FIG. 6 a sample humidity signal characteristic measured by a mobile phone according to an embodiment of the present invention, and FIG. 7 a flow diagram of a method for operating a mobile phone according to an embodiment of the present invention.

DETAILED DESCRIPTION OF THE INVENTION

Figure 1:
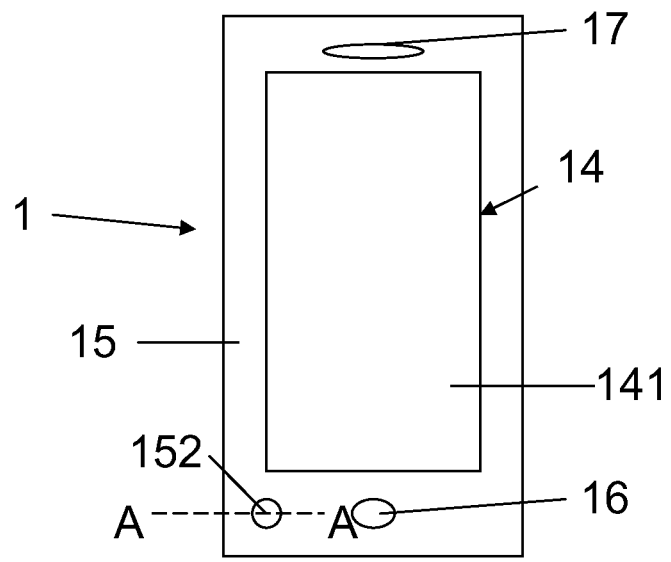

FIG. 1 illustrates a schematic diagram of a top view of a mobile phone according to an embodiment of the present invention. The mobile phone 1 includes a standard microphone 16, a standard speaker 32, and an output unit 14 in form of a display 141. In addition, the mobile phone 1 comprises a window 152 in a casing 15 of the mobile phone 1.

Figure 2:
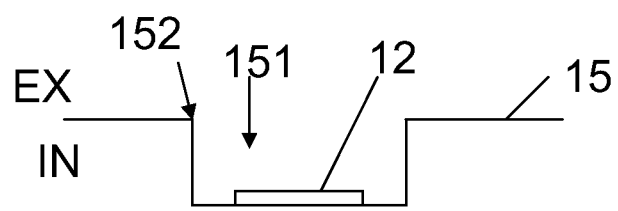
Figure 2:
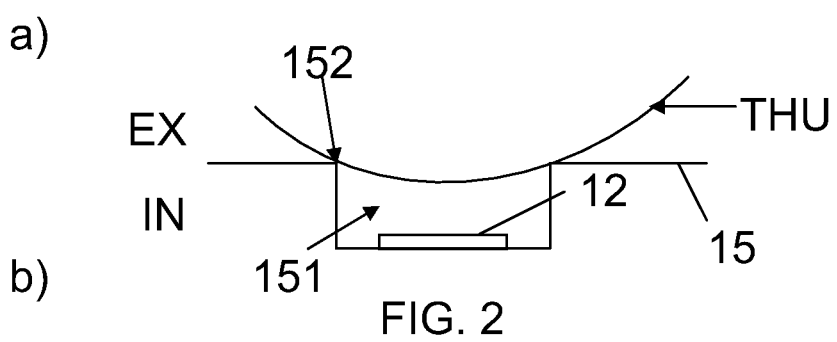

FIG. 2a) illustrates a side cut of a cavity 151 arranged in the casing 15 underneath the window 152 along lines A-A in FIG. 1. The cavity 151 takes the shape of a recess and is formed by leak-proof walls of the casing 15. The window 152 connects the cavity 151 to an exterior EX of the casing 15. At the bottom of the cavity 151 a humidity sensor 12 is arranged for measuring the humidity in the cavity 151. The humidity sensor 12 may be arranged on a substrate building at least a part of the bottom of the cavity 151.

In the scenario depicted in FIG. 2a) the humidity in the cavity 151 may more or less be equal to the humidity prevailing in the exterior EX of the mobile phone 1, i.e. in its environment. The window 152 allows for an interchange of air between the exterior EX and the cavity 151.

In FIG. 2b), the cavity of FIG. 2a) is depicted again, however, now in a different usage scenario: It is assumed, that a user covers the window 152 in the casing 15 with a part of the skin such as his/her thumb THU. In doing so, the volume of the cavity 151 becomes disconnected from the exterior EX of the mobile phone 1 such that the humidity in the cavity 151 may be dominated by humidity resulting from a trans-epidermal water loss through the users skin at his/her thumb THU. In such scenario, the cavity 151 is hermetically sealed versus the exterior by means of the thumb THU covering the window, and versus an interior IN of the casing 15, by means of the cavity walls.

Of course, the effect of separating the cavity 151 from the exterior EX and making the humidity in the cavity 151 be dominated by the trans-epidermal water loss may also hold for the user covering the window 152 with any other part of the body, such as, for example, with the cheek when holding the mobile phone 1 just as for calling. While the user covers the window 152 with a part of the body, the humidity in the cavity 151 first rises in response to such trans-epidermal water loss and then saturates.

A humidity signal RH(t) supplied by the humidity sensor 12 may reflect such change in humidity in the cavity 151. According to FIG. 4, which illustrates a block diagram of a mobile phone 1 according to an embodiment of the present invention, such humidity signal RH(t) is supplied by the humidity sensor 12 to a control unit 11 of the mobile phone 1 where the humidity signal RH(t) is analyzed. The control unit 11 may be implemented by means of a logic, software or other means. The analysis may be focused on deriving information from the humidity signal RH(t), and in particular from its characteristics over time, i.e. its dynamics, on properties of the users skin, and specifically on a humidity status of the skin. Such information may then be presented to the user via the output unit 14. Symbolically, signal C(t) issued by the control unit 11 to the output unit 14 represents such information to be output to the user.

Figure 6:
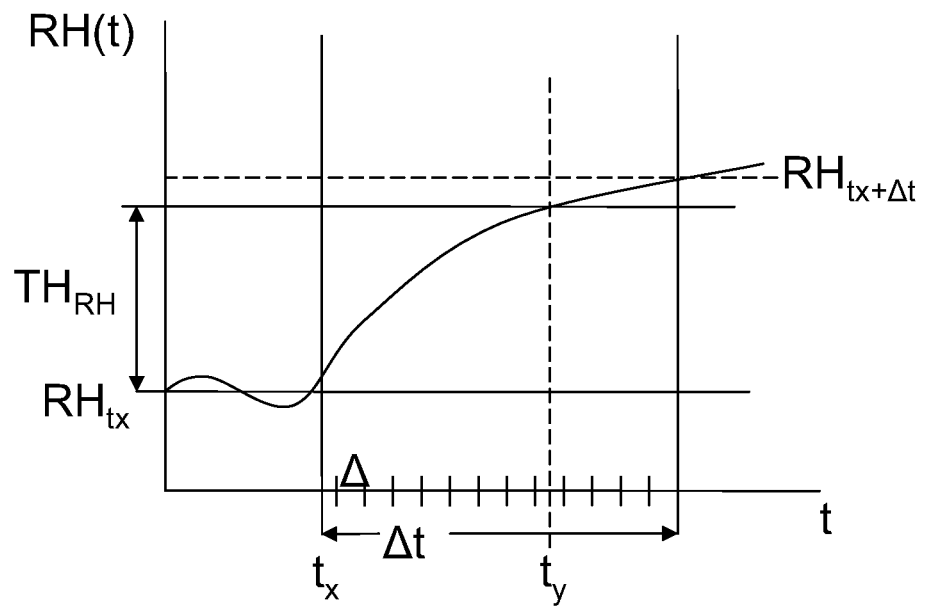

Switching to FIG. 6, a sample relative humidity characteristic RH(t) over time t is depicted. It is assumed that for $t<t_x$, the window 152 in the casing 51 is not covered such that the humidity sensor 12 essentially detects the humidity of the exterior EX of the mobile phone 1. It is assumed, that at $t=t_x$ the user of the mobile phone triggers the skin humidity analysis function and more or less simultaneously covers the window 152 with a part of the skin such as his/her thumb and thereby closes the cavity 151.

The trigger may be set by the user by pressing a key, a touch key, or by means of any other human-machine interface assigned. At the time of the trigger $t_x$, the current humidity value $RH(t_x)=RH_{tx}$ is measured and stored in a memory of the mobile phone 1 as reference humidity value $RH_{tx}$. Such reference humidity value $RH_{tx}$ preferably represents the humidity of the environment of the mobile phone but not any human induced humidity.

In a first embodiment of the analysis, the subsequent dynamics of the humidity signal RH(t) is analyzed, for example, by means of determining the first or any higher order derivative of the humidity signal RH(t), or by means of determining a response time of the humidity signal RH(t).

In another embodiment of the analysis, it may be investigated, at which point in time $t_y$ relative to the trigger point in time $t_x$ a change in humidity ARH with respect to the reference humidity value $RH_{tx}$ reaches a given target change $TH_{RH}$, i.e. $RH(t_y)=>RH_x+TH_{RH}$. If, for example, a new humidity signal value RH is supplied every $\Delta$st seconds, for example, every 500 ms, at each such supply time $t=t_x+m\Delta$st with m being an integer, it is determined if $RH(t_x+m\Delta st)-RH_x=>TH_{RH}$. At a certain point in time $t_y$, see in the diagram of FIG. 6, this condition is fulfilled and the determined time $t_y$ may be classified and allow for a conclusion on the humidity balance of the user's skin.

In a further embodiment, the analysis may encompass that a defined time interval $\Delta t$ is started at the trigger point in time $t_x$. In the present analysis it is of interest which humidity value is reached after the given time interval $\Delta t$, i.e. at point in time $t=t_x+\Delta t$. In the present example in FIG. 6, the humidity value $RH(t_x+\Delta t)=RH_{tx+\Delta t}$ is determined at the end of such time interval. By means of subtracting the reference humidity value $RH_x$ from the such humidity value $RH_{tx+\Delta t}$, a change in humidity $\Delta RH=RH_{tx+\Delta t}-RH_x$ over time interval $\Delta t$ is determined and may serve for assigning a skin humidity class to the user's skin, for example, such as "dry skin". Such result may be presented to the user via the output unit 14, for example in form of characters or a symbol displayed on the display. In this respect, the dynamics in the humidity signal may allow for a conclusion on the humidity properties of the skin. For example, the higher the change in humidity $\Delta RH=RH_{tx+\Delta t}-RH_{tx}$ is within the time interval $\Delta t$ the more humidity may be evaporated into the cavity 151. This may lead to a conclusion that the user's skin may be of sufficient humidity property. In addition to the change in humidity $\Delta RH=RH_{tx+\Delta t}-RH_{tx}$, the classification may be determined by the absolute humidity value $RH_{tx+\Delta t}$ reached at the end of the time interval $t=t_x+\Delta t$.

Preferably, when the end of the time interval $\Delta t$ is reached, i.e. at $t=t_x+\Delta t$, an acoustic signal such as a beep may be issued in order to make the user aware that the measurement is terminated and he/she no longer needs to cover the window 152.

The humidity signal RH(t) in FIG. 6, represents a usage scenario in which the trigger may coincide with the window in the casing being covered with a body part. A subsequent increase of the relative humidity in the cavity may be detected. In a different usage scenario, the user may cover the window with a body part prior to any trigger. At the time of the trigger the body part may be removed from the window.

Subsequently, the air in the cavity which is enriched with the humidity stemming from the trans-epidermal water loss may escape into the exterior such that the measured relative humidity in the cavity drops. Such drop is detected and analyzed in the following. Preferably, at trigger time $t=t_x$ the associated humidity level is recorded, and the subsequent dynamics in the humidity signal is investigated.

Figure 7:
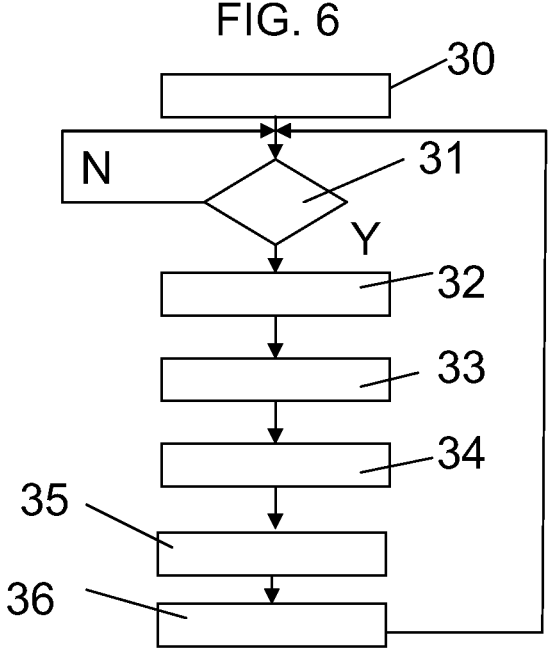

A method similar to the ones previously described is illustrated in the flow chart of FIG. 7. In a first step 30, the method is started. The starting step may involve, for example, switching on the mobile phone. In step 31, it is verified, if the user has triggered a humidity determination process, e.g. by pressing a key of the mobile phone. In case the user has not yet triggered such process (N), it is continuously waited for such trigger signal. In case the user has triggered such process (Y), the humidity of the skin of the user will be determined in the following and be presented to the user. Alternative to step 31, the process may wait for an interrupt as trigger signal for starting the subsequent measurement and analysis steps.

In step 32, the current humidity value is determined and stored as a reference humidity value. In step 33 a derivative of the humidity signal is determined. Optionally, in step 34 additional information may be extracted from the humidity signal RH(t) if needed. In step 35, the derivative is compared to one or more thresholds for classifying the measuring result, for example, by means of assigning a humidity class to the measuring result. In step 36, such classification result is presented to an output unit of the mobile phone. By such step, the process returns back to step 31 for being prepared for a new measurement and analysis.

Subject to the way the humidity signal is analyzed, the step 35 may have different analysis content, and eventually, step 33 may prepare an analysis in a different way.

Referring back to FIG. 4, according to another embodiment, the mobile phone 1 may include a temperature sensor 13 for supplying a temperature signal T(t) to the control unit 11. The temperature sensor 13 may be arranged to measure a temperature of the user's skin when covering the cavity 151 with a body part. In such scenario, a region of the casing 15 close to the window 152 may be touched by the user where a temperature sensor or a heat conducting element is arranged. According to the side cut of a cavity 151 according to FIG. 3, such heat conducting element 131 may include a pad shaped platform close to the window 152 arranged at the outer surface of the casing 15 for interacting with the user's skin when the user covers the window 152 for a skin humidity measurement. Such pad may be connected via a wire like structure to a temperature sensor 13 arranged at the bottom of the cavity 151 together with the humidity sensor 12, for example. The temperature sensor 13 and the humidity sensor 12 may be arranged on a common substrate not shown. By way of touching the heat conducting element 131, body heat may be transferred to the temperature sensor 13 and there be converted into a temperature signal T(t). Such temperature signal T(t) may be supplied to the control unit 11 according to FIG. 4. The control unit 11 may analyze the temperature signal T(t), and/or may simply present the measured temperature on the display 141 of the mobile phone, for example. The process of measuring the temperature signal T(t) may be triggered by the user by pressing a key or a touch key, or may automatically be triggered synchronously with the humidity measurement, or it may be triggered independent thereof.

Figure 3:
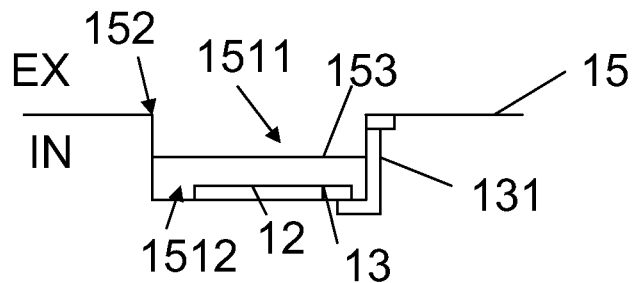

In addition, the cavity 151 may be separated into two volumes 1511 and 1512 by an air permeable membrane 153 as shown in FIG. 3. The humidity sensor 12 is arranged for measuring the humidity in the second volume 1512 which is confined, in the present example, by cavity walls, the humidity sensor or its substrate respectively, and the membrane 153, while the first volume 1511 is connected to the window 152. The membrane 153 may act as a low pass filter with respect to the humidity which is beneficial for small cavity volumes for preventing swift changes in the humidity signal. Hence, the effect evoked by the membrane may be desired for making the measurement become more accurate.

Figure 4:
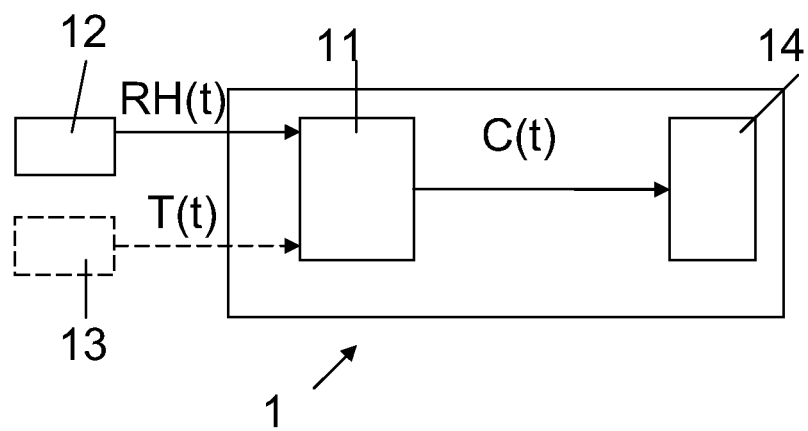
Figure 5:
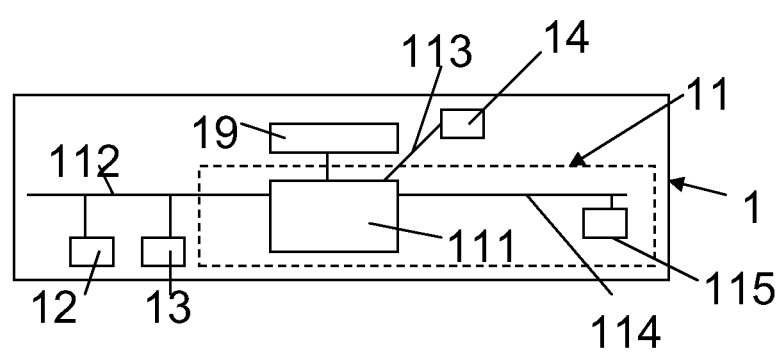

FIG. 5 shows a schematic hardware oriented block diagram of a mobile phone 3 according to an embodiment of the present invention. Here, the processing as illustrated in connection with FIGS. 4 and 6 is implemented as software residing in a memory 115 connected to a microprocessor 111 via a system bus 114, and will be executed by the microprocessor 111 on demand. The humidity sensor 12 and the temperature sensor 13 are connected to the microprocessor 111 via an input system bus 112. In addition, there is shown a wireless interface 19 of the mobile phone 1. The output unit 14 is connected to the microprocessor 111 via an output system bus 113. The control unit 11 may include elements within the dashed rectangle. In the present example, the control unit 11 is merged with the overall control unit of the mobile phone 1.

While there are shown and described presently preferred embodiments of the invention, it is to be distinctly understood that the invention is not limited thereto but may be otherwise variously embodied and practised within the scope of the following claims.

The invention claimed is:

1. A mobile phone, comprising
a casing and a cavity in the casing, the cavity being in the shape of a recess, sealed from an interior of the casing by cavity walls and connected to the exterior of the casing by a window in the casing,
a humidity sensor disposed in the cavity and arranged for measuring a humidity in the cavity, wherein the humidity sensor comprises a sensitive element, said sensitive element comprising a layer for accepting water molecules from the air in the cavity,
a control unit for analyzing a humidity signal supplied by the humidity sensor, and
an output unit for presenting a result of the analysis.

2. The mobile phone according to claim 1, comprising
a window in the casing, said casing connecting the cavity to an exterior of the casing,
wherein the cavity is arranged for receiving a humidity resulting from a transepidermal water loss when a body part of the user covers the window.

3. The mobile phone according to claim 1, comprising
a membrane permeable to air arranged in the cavity, said membrane separating the cavity into a first volume and a second volume,
wherein the first volume is connected to the window and the second volume is confined by the membrane and cavity walls, and
wherein the humidity sensor is arranged for measuring the humidity in the second volume.

4. The mobile phone according to claim 1, comprising
a temperature sensor arranged for measuring a temperature of a body part of a user when the body part covers the window, and
in particular comprising a heat conducting element, said heat conducting element conducting heat from a surface of the casing to the temperature sensor arranged on a common carrier together with the humidity sensor.

5. The mobile phone according to claim 1, wherein the control unit is configured for analyzing a characteristic of the humidity signal over time.

6. The mobile phone according to claim 5, wherein the control unit is configured for determining one of
- a derivative of the humidity signal,
- a change of the humidity signal within a given time interval, and
- a point in time at which a given target change of the humidity signal is achieved.

7. The mobile phone according to claim 1, comprising means for triggering the analysis of the humidity signal.

8. The mobile phone according to claim 5, comprising means for triggering the analysis of the humidity signal, wherein the control unit is configured for
- storing a present humidity value as a reference humidity value in response to a trigger of the analysis,
- determining a skin humidity class subject to the analysis of the characteristic of the humidity signal over time, and
- initiating a presentation of the skin humidity class via the output unit.

9. The mobile phone according to claim 1, wherein the control unit is configured for determining a skin humidity class subject to a change in the humidity signal and subject to a humidity value reached at the end of a given time interval.

10. The mobile phone according to claim 1, wherein the output unit includes a display, and wherein the result is presented on the display.

11. A method for operating a mobile phone, comprising the steps of
using a layer of a sensitive element of a humidity sensor disposed in a cavity of a casing of the mobile phone and arranged for measuring a humidity in the cavity, wherein the humidity sensor comprises a sensitive element comprising a layer for accepting water molecules from air in the cavity, the cavity being in the shape of a recess, sealed from an interior of the casing by cavity walls and connected to the exterior of the casing by a window in the casing,
analyzing a humidity signal supplied by the humidity sensor, and
presenting a result of the analysis via an output unit of the mobile phone in response to a trigger.

12. The method of claim 11, further comprising the step of analyzing an increase in the humidity signal in response to the trigger.

13. The method of claim 11, further comprising the step of analyzing a decrease in the humidity signal in response to the trigger.

14. A non-transitory computer-readable medium having a computer program element embodied therein in form of a plurality of instructions,
wherein the plurality of instructions, when executed by a microprocessor, implements a method according to claim 11.

* * * * *